(12) United States Patent
Cao et al.

(10) Patent No.: US 10,085,761 B2
(45) Date of Patent: Oct. 2, 2018

(54) TOOL BIT OF ULTRASONIC OSTEOTOME AND ULTRASONIC OSTEOTOME INCLUDING THE SAME

(71) Applicants: Qun Cao, Beijing (CN); Chunyuan Li, Beijing (CN)

(72) Inventors: Qun Cao, Beijing (CN); Chunyuan Li, Beijing (CN)

( * ) Notice: Subject to any disclaimer, the term of this patent is extended or adjusted under 35 U.S.C. 154(b) by 176 days.

(21) Appl. No.: 14/997,726

(22) Filed: Jan. 18, 2016

(65) Prior Publication Data

US 2016/0128711 A1 May 12, 2016

Related U.S. Application Data

(63) Continuation of application No. PCT/CN2014/079578, filed on Jun. 10, 2014.

(30) Foreign Application Priority Data

Jul. 22, 2013 (CN) .................... 2013 2 0435087 U (51) Int. Cl.
*A61B 17/32* (2006.01)
*A61B 17/3209* (2006.01)
(Continued)

(52) U.S. Cl.
CPC .. *A61B 17/320068* (2013.01); *A61B 17/1604* (2013.01); *A61B 17/1659* (2013.01); *A61B 17/32* (2013.01); *A61B 17/3205* (2013.01); *A61B 17/3209* (2013.01); *A61B 2017/32007* (2017.08); *A61B 2017/320072* (2013.01); *A61B 2017/320074* (2017.08); *A61B 2017/320075* (2017.08); *A61B 2217/007* (2013.01)

(58) Field of Classification Search
CPC . A61B 17/1604; A61B 17/1659; A61B 17/32; A61B 17/320068; A61B 2017/320072; A61B 2017/320074; A61B 2017/320075; A61B 17/3205; A61B 17/3209
See application file for complete search history.

(56) References Cited

U.S. PATENT DOCUMENTS 5,318,570 A 6/1994 Hood et al.
5,674,235 A 10/1997 Parisi
(Continued)

FOREIGN PATENT DOCUMENTS

CN 1745721 A 3/2006
CN 200942107 Y 9/2007
(Continued)

OTHER PUBLICATIONS

Australian Patent Examination Report No. 1 for Australian patent application No. 2014295670; Australian Government; IP Australia; dated Oct. 24, 2016.
(Continued)

*Primary Examiner* — Larry E Waggle, Jr.
(74) *Attorney, Agent, or Firm* — Thomas E. Lees, LLC (57) ABSTRACT

A tool bit (100) of an ultrasonic osteotome includes: an arbor (2); and an end portion (1) of the tool bit connected to a front end of the arbor (2). The end portion (1) of the tool bit has a spoon-like shape and has a toothed front edge. An ultrasonic osteotome including the tool bit is also provided.

11 Claims, 6 Drawing Sheets

(51) Int. Cl.
  *A61B 17/16* (2006.01)
  *A61B 17/3205* (2006.01)

(56) References Cited

U.S. PATENT DOCUMENTS

| | | | |
|---|---|---|---|
| 5,695,510 A | 12/1997 | Hood | |
| 6,267,594 B1 | 7/2001 | Hugo | |
| 6,497,715 B2 * | 12/2002 | Satou | A61B 17/32006 604/22 |
| 8,512,340 B2 * | 8/2013 | Easley | A61B 17/1659 606/79 |
| 2004/0023187 A1 * | 2/2004 | Hickok | A61C 3/03 433/119 |
| 2010/0057118 A1 | 3/2010 | Dietz et al. | |
| 2011/0270256 A1 | 11/2011 | Nelson et al. | |
| 2013/0184711 A1 | 7/2013 | Rad | |
| 2013/0204285 A1 * | 8/2013 | Gouery | A61B 17/32006 606/169 |
| 2014/0163595 A1 * | 6/2014 | Witt | A61B 17/32006 606/169 |

FOREIGN PATENT DOCUMENTS

| | | | |
|---|---|---|---|
| CN | 201404264 Y | 2/2010 | |
| CN | 102143715 A | 8/2011 | |
| CN | 202146339 U | 2/2012 | |
| CN | 202821533 U * | 3/2013 | A61B 17/1604 |
| CN | 103431894 A | 12/2013 | |
| CN | 203354612 U | 12/2013 | |
| EP | 0456470 A1 | 11/1991 | |
| EP | 1736107 A1 | 12/2006 | |
| JP | 2006-263031 A | 10/2006 | |
| JP | 2012-501735 A | 1/2012 | |
| WO | 2006059120 A1 | 6/2006 | |
| WO | 2014088899 A1 | 6/2014 | |

OTHER PUBLICATIONS

Korean Patent Examination Report for Korean patent application No. KR20-2016-7000007; Korean Patent Office; dated Jan. 10, 2017.
Supplementary European Search Report for European patent application No. 14828953.1; European Patent Office; dated Dec. 8, 2016.
Written Opinion of the International Searching Authority for PCT Application No. PCT/CN2014/079578; dated Jul. 29, 2014.
International Search Report for PCT Application No. PCT/CN2014/079578; dated Jul. 29, 2014; State Intellectual Property Office of the P. R. China; Beijing, China; English translation included.

* cited by examiner

TOOL BIT OF ULTRASONIC OSTEOTOME AND ULTRASONIC OSTEOTOME INCLUDING THE SAME

CROSS REFERENCE TO RELATED APPLICATIONS

This is a Continuation application of International Application Serial No. PCT/CN2014/079578 filed on Jun. 10, 2014, which claims the benefit of Chinese Application No. 201320435087.6 filed on Jul. 22, 2013, the disclosures of which are hereby incorporated by reference.

BACKGROUND

1. Field of the Invention

The present disclosure relates to a technical field of medical equipment, in particular to an improved tool bit of ultrasonic osteotome and an ultrasonic osteotome comprising the tool bit.

2. Description of the Related Art

Conventional orthopedic equipments such as an electric drill and ultrasonic osteotome apply downward forces in most of operations in surgery, which may bring great risk.

Figure 1A:
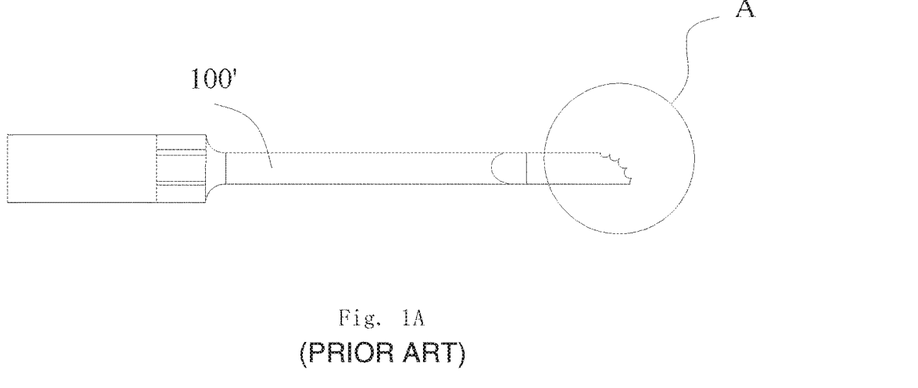
FIG. 1A is a schematic view showing a structure of a tool bit of an ultrasonic osteotome in the prior art.
Figure 1B:
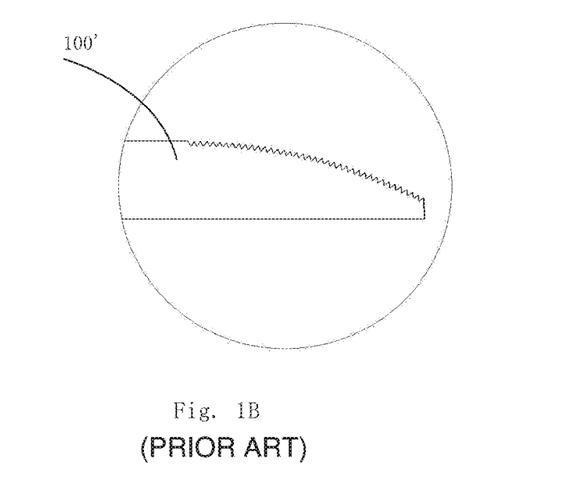
FIG. 1B is a local enlarged schematic view of part A shown in FIG. 1A.

FIG. 1A shows a typical structure of a conventional tool bit 100' of ultrasonic osteotome, which has a plurality of teeth and a wide tip. However, a majority part of the tip does not constitute an effective main cutting part, as shown in FIG. 1B.

Figure 2A:
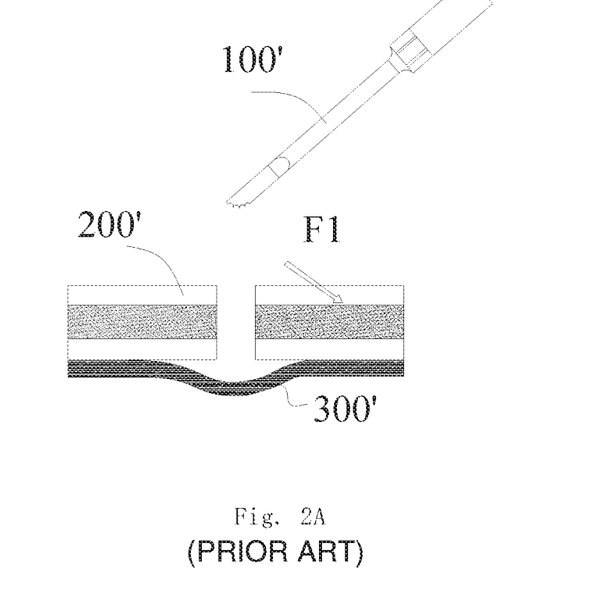
FIGS. 2A-2B are schematic views showing operations of the tool bit of the ultrasonic osteotome in the prior art.
Figure 2B:
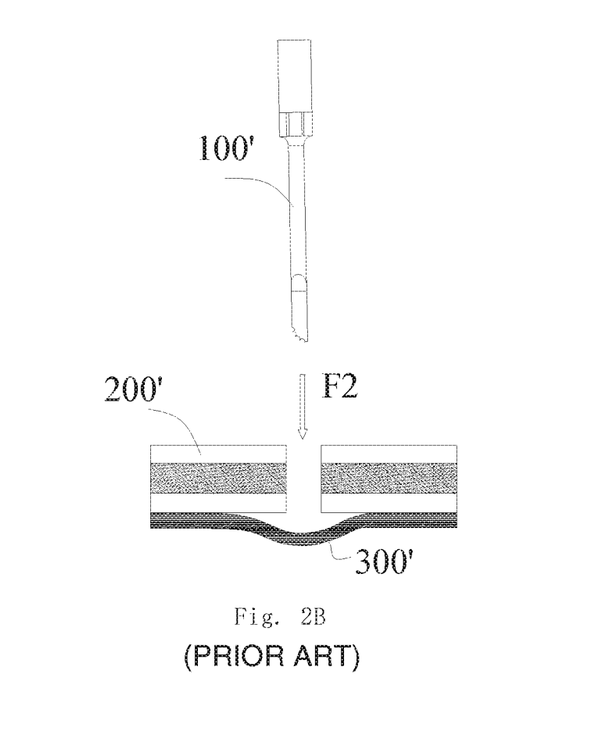

The tool bit 100' also has the following defects. As illustrated in FIG. 2A, when the tool bit 100' is used, a force needs to be applied to osseous tissue of a bone 200', as indicated by F1 in FIG. 2A. When the cutting operation is desired, the tool bit 100' needs to apply the force downwardly to the osseous tissue, which may not only cause a low cutting speed and a low efficiency, but also cause the tool bit with a plurality of teeth to break in operation, as indicated by F2 in FIG. 2B. Further, as illustrated in FIGS. 2A and 2B, soft tissue 300' below the cutting location is invisible. As the force is applied downwardly in operation, it tends to destroy the tissues which are located below the cutting location and are undesired to be injured. In this way, the risk of surgery may be increased significantly, chance of success in surgery may be reduced, and operation difficulty of a doctor may be increased. For example, in a backbone surgery, typically, the spinal cord is just located below the surgical site for the backbone surgery. If the spinal cord is injured, the patient will at least lose a function, be permanently paralysed, even decease.

BRIEF SUMMARY

In order to solve at least one of the above problems in the prior art, the present disclosure provides a tool bit of an ultrasonic osteotome that has a high efficiency and a high cutting speed to reduce the time required for surgery.

Further, the present disclosure provides a tool bit of an ultrasonic osteotome that may be positioned correctly in cutting operation to improve the chance of success in surgery.

Further, the present disclosure also provides an ultrasonic osteotome including the tool bit as described above.

In accordance with an embodiment, a tool bit of an ultrasonic osteotome comprises: an arbor; and an end portion of the tool bit connected to a front end of the arbor, wherein the end portion of the tool bit has a spoon-like shape and has a toothed front edge.

The tool bit according to an embodiment of the present invention, may increase the cutting speed to reduce the time required for surgery, and may be positioned correctly in cutting operation without skidding to improve the chance of success in surgery.

In addition, the tool bit according to an embodiment of the present invention may also comprise the following additional technical features:

In an embodiment, the front edge of the end portion of the tool bit has a maximum width not less than the width of the arbor.

In an embodiment, both the arbor and the end portion of the tool bit have hollow inner chambers that are communicated with each other.

In an embodiment, the end portion of the tool bit is formed with a bore(s) which is(are) located in at least one of the spoon center and the spoon bottom of the end portion of the tool bit and is(are) in communication with the hollow inner chambers.

In an embodiment, the tool bit further comprises: a bit body connected to a rear end of the arbor, wherein the arbor and the bit body are of cylindrical shape, the bit body has a cylindrical dimension greater than that of the arbor, and the bit body and the arbor are connected via an arc transition.

In an embodiment, the bit body is provided with a wrench-operation position.

In an embodiment, a screwed connection hole is formed on the side of the bit body opposed to the arbor and is communicated with the hollow inner chambers.

In an embodiment, the front edge of the end portion of the tool bit is formed with a plurality of tooth slots substantially extending in a direction from a concave surface of the end portion of the tool bit to a convex surface thereof.

In an embodiment, each of the tooth slots is at an angle of less than 90 degrees with respect to the direction from the concave surface of the end portion of the tool bit to the convex surface thereof.

In an embodiment, each of the tooth slots has an end in communication with the concave surface of the end portion of the tool bit, and has a length in width direction reduced gradually from a central part to two lateral parts.

In an embodiment, at least one of two opposed side walls of the end portion of the tool bit connected to the convex surface and the concave surface respectively is provided with a plurality of first grooves spaced from each other.

Preferably, each of the first grooves extends in a direction from a spoon center to a spoon bottom and the plurality of first grooves are distributed in a direction from the front to the rear.

In some embodiments, a convex surface of the end portion of the tool bit is provided with a plurality of second grooves.

Preferably, each of the second grooves extends in the width direction of the end portion of the tool bit and the plurality of second grooves are distributed in a direction from the front to the rear.

An embodiment of the present invention also provides an ultrasonic osteotome comprising the tool bit according to any one of the above embodiments.

Such design of the ultrasonic osteotome according to the embodiment of the present invention, not only may increase the cutting speed to reduce the time required for surgery, but also may be positioned correctly in cutting operation without skidding to improve the chance of success in surgery.

BRIEF DESCRIPTION OF THE SEVERAL VIEWS OF THE DRAWINGS

The above and/or additional aspects and advantages of the present disclosure will be understood more apparently from the following description of embodiments with reference to the accompanied figures, in which.

DETAILED DESCRIPTION

The specific embodiments of the present invention will be described in detail below with reference to accompanied figures. Throughout the description, identical or similar reference numerals represent identical or similar members. It should be noted that embodiments described herein are depicted only for illustration, instead of limiting to the present invention.

In the description of the present disclosure, it should be noted that the orientations or positions represented by the terms of "up", "down", "vertical", "horizontal", "top", "bottom", "inner" and "outer" and the like are based on the figures. It is given only by way of examples, instead of being intended to limit the device or element to have a special orientation or to be configured and operated in a special orientation. Thus, it cannot be understood as limiting of the present invention. In addition, the terms of "first" and "second" are depicted only by illustration, instead of being intended to define which one is more important or to define the number of the technical features. Thereby, the features defined by the terms of "first" and "second" may literally or impliedly include one or more features. In the description of the present disclosure, the term of "a plurality of" means two or more, unless it is explained otherwise.

In the description of the present disclosure, it should be noted that the terms of "mount", "connect" and "couple" should be understood in broad sense, unless they are defined or provided otherwise. For example, they may be used to describe a fixed connection, or a dismountable connection or an integral connection; they may be used to describe a mechanical connection, an electrical connection; they may be used to describe direct connection or connection by intermediate medium, or communication between interiors of two elements. The specific significations of the above terms in the present disclosure may be understood in the context by the skilled person in the art.

The technical solutions of the present disclosure will be further explained below with reference to figures and embodiments.

Figure 3:
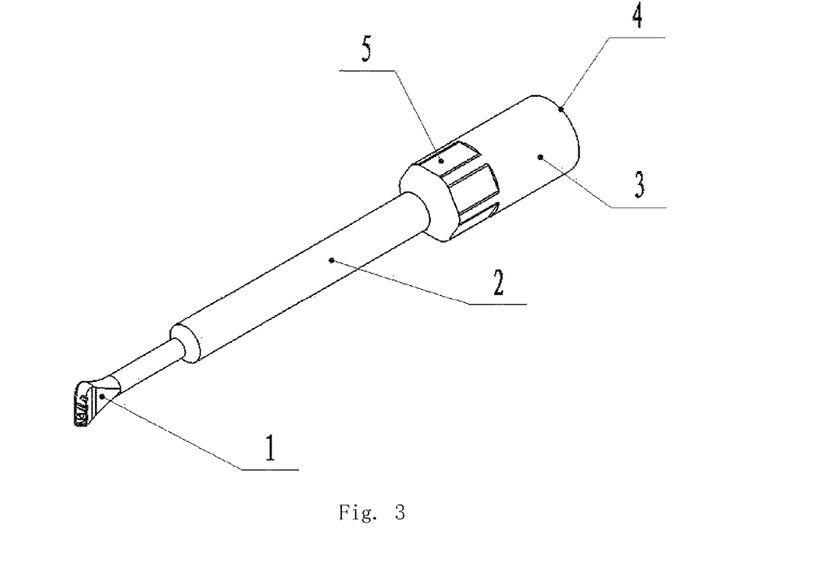
FIG. 3 is a schematic view showing a perspective structure of a tool bit of an ultrasonic osteotome in accordance with an embodiment of the present invention.
Figure 4:
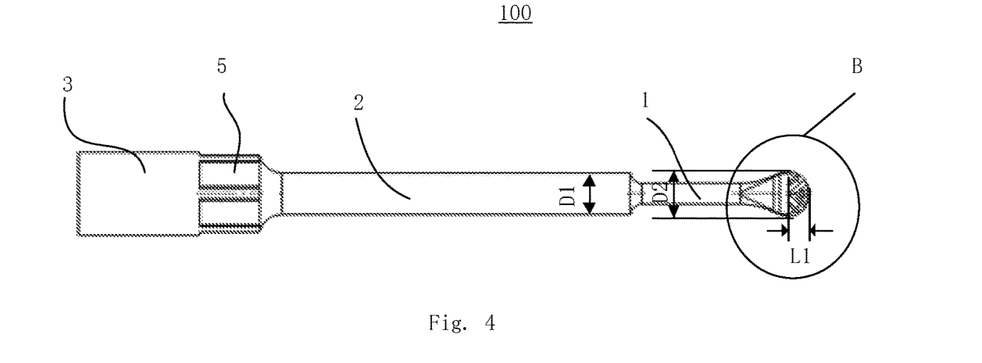
FIG. 4 is a top view of the tool bit of the ultrasonic osteotome in accordance with an embodiment of the present invention.
Figure 5:
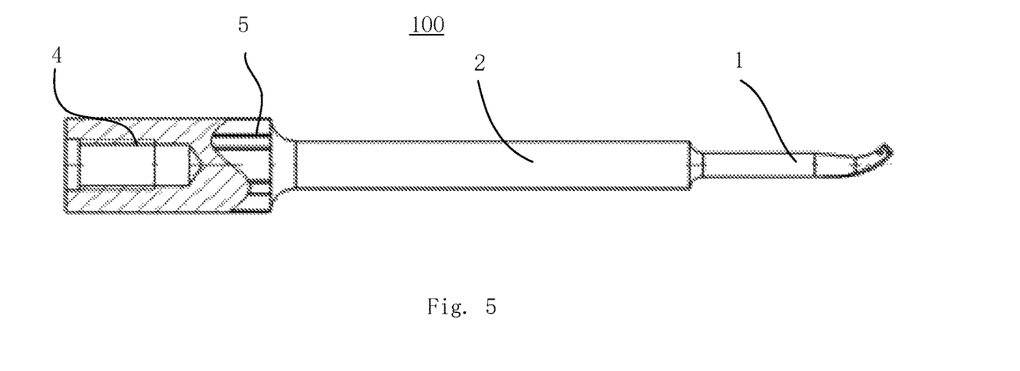
FIG. 5 is a front view of the tool bit of the ultrasonic osteotome in accordance with an embodiment of the present invention.
Figure 6:
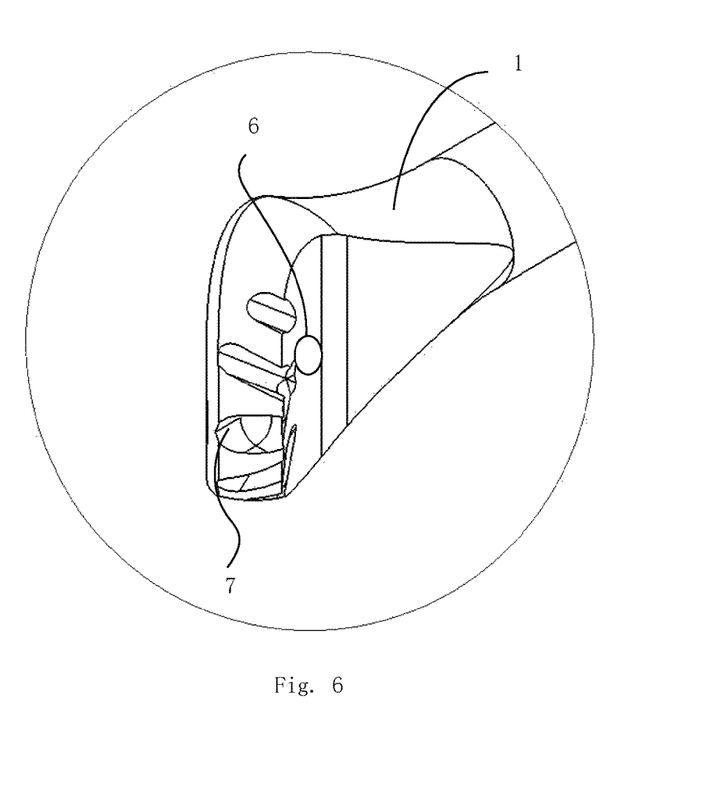
FIG. 6 is a schematic view showing a local enlarged structure of part B shown in FIG. 3.

A tool bit of an ultrasonic osteotome in accordance with an embodiment of the present invention will be described below with reference to figures. FIG. 3 is a schematic view showing a perspective structure of a tool bit 100 of an ultrasonic osteotome in accordance with an embodiment of the present invention. FIG. 4 is a top view of the tool bit 100 of the ultrasonic osteotome in accordance with an embodiment of the present invention. FIG. 5 is a front view of the tool bit 100 of the ultrasonic osteotome in accordance with an embodiment of the present invention. FIG. 6 is a schematic view showing a local enlarged structure of part B shown in FIG. 4.

As illustrated in FIG. 3, in accordance with an embodiment of the present invention, the tool bit 100 of the ultrasonic osteotome may include an end portion 1 of the tool bit and an arbor 2. The end portion 1 of the tool bit is connected to a front end of the arbor 2. The end portion 1 of the tool bit has a spoon-like shape and has a toothed front edge. Such design may increase the cutting speed to reduce the time required for surgery. Further, it may be positioned correctly in cutting operation without skidding, so as to improve the chance of success in surgery.

As illustrated in FIG. 3, a bit body 3 is connected to the arbor 2. The arbor 2 is an elongate cylindrical section whereas the bit body 3 is a cylindrical section relatively shorter in length than a length of the arbor 2. The bit body 3 and the arbor 2 are connected via an arc transition. The bit body 3 is provided with a wrench-operation position 5 thereon. A threaded connection hole 4 is formed on the side of the bit body 3 opposed to the arbor 2. The threaded connection hole 4 is configured to be connected in thread with an ultrasonic transducer (not shown). When it needs to be used, the threaded connection hole 4 at a rear end of the tool bit is connected to a special ultrasonic transducer, and the connection is tighten by a corresponding wrench at the wrench-operation position 5. And then the ultrasonic transducer is connected to a special ultrasonic machine and thereby an ultrasonic cutting may be available.

In accordance with an embodiment of the present invention, the front edge of the end portion 1 of the tool bit 100 has a maximum width D2 being not less than the width D1 of the arbor 2. Such structure has an advantage that the cutting width of the end portion 1 of the tool bit is greater than or equal to the diameter of the arbor 2 in use. In surgery, when a thicker bone or a deeper groove or window-type incision is cut, it may prevent the tool bit from being jammed while ensuring water to pour to the cutting position of the end portion of the tool bit, so as to prevent the incision from being burned.

In accordance with an embodiment of the present invention, both the arbor 2 and the end portion 1 of the tool bit 100 have hollow inner chambers that are communicated with each other. The end portion 1 of the tool bit has a bore which is located in the spoon center. Such design may have an advantage that the tool bit with single outlet at the spoon center may ensure the poured liquid to pass through the hollow chamber to the spoon center and to flow out of the tool bit. In this way, in surgery, the spoon center, the entire end portion 1 of the tool bit and the tissue they contact with may be cleaned and cooled by the poured liquid in real time completely, so as to ensure the removed bone crumbs to be discharged timely. Thus, there is a clear and clean view at the incision and the tissue to be remained is protected from being damaged, which is particularly noticeable in scraping operation. In this way, the surgery risk will be further reduced, and the safety together with the chance of success in surgery will be improved.

In accordance with an embodiment of the present invention, both the arbor 2 and the end portion 1 of the tool bit 100 have hollow inner chambers that are communicated with each other. The bore 6 of the end portion 1 of the tool bit may be located in the spoon center, i.e., the bore 6 is arranged on the concave surface, as illustrated in FIG. 6. Such design may have an advantage that the tool bit with single outlet at the spoon center may ensure the poured liquid to pass through the hollow chamber to the spoon center and to flow out of the tool bit. In this way, in surgery, the spoon center, the entire end portion 1 of the tool bit and the tissue they contact with may be cleaned and cooled by the poured liquid in real time completely, so as to ensure the removed bone crumbs to be discharged timely. Thus, there is a clear and clean view at the incision and the tissue to be remained is protected from being damaged, which is particularly noticeable in scraping operation (indicated by F4 in FIG. 9). In this way, the surgery risk will be further reduced, and the safety together with the chance of success in surgery will be improved.

In accordance with an embodiment of the present invention, the bore 6 may also be arranged at the spoon bottom, i.e., the convex surface is provided with the bore 6 thereon. In accordance with an embodiment of the present invention, the end portion 1 of the tool bit may have two bores 6 that are located at the spoon center and the spoon bottom respectively. Such design has an advantage that the tool bit 100 with two outlets at the spoon center and spoon bottom may ensure that the poured liquid flows out from both the spoon center and the spoon bottom. In surgery, the spoon center, the spoon bottom, the entire end portion of the tool bit and the tissues that they contact with may be cleaned and cooled by the poured liquid in real time completely, so as to ensure the removed bone crumbs to be discharged timely. Because water flows out from both up and down locations, there is a clear and clean view at the incision and the tissue to be remained is protected more advantageously from being damaged. It is particularly advantageous when the end portion of the tool bit with the spoon-like shape is extended into between the spinal dural and the vertebral body (bone) to be removed and a force is applied in a direction from inside to outside, because the water flowing out from the spoon bottom may protect the spinal dural and the spinal cord below the spoon bottom and the water flowing out from the spoon center may protect the tissue above the spoon center. Further, when one outlet is blocked or jammed in surgery, the other outlet may still allow the liquid to flow out sufficiently to provide the protection. In addition, the arrangement of two outlets allows the liquid to flow to the tissue more sufficiently. As has been discussed above, in this way, the surgery risk will be further reduced, and the safety together with the chance of success in surgery will be further improved.

With a brief reference to FIG. 6, and in accordance with an embodiment of the present invention, the front edge of the end portion 1 of the tool bit is formed with a plurality of tooth slots 7 substantially extending in a direction from a concave surface of the end portion 1 of the tool bit to a convex surface thereof. Each of the tooth slots 7 is substantially at an angle of less than 90 degrees with respect to the direction from the concave surface of the end portion 1 of the tool bit to the convex surface thereof. As illustrated in FIG. 6, each of the tooth slots 7 has an end in communication with the concave surface of the end portion 1 of the tool bit, and has a length L1 in width direction reduced gradually from a central part to two lateral parts. In this way, the teeth with various sizes between adjacent tooth slots 7 may be used to perform the surgery operation, which may be selected easily by the surgery operator.

Figure 7:
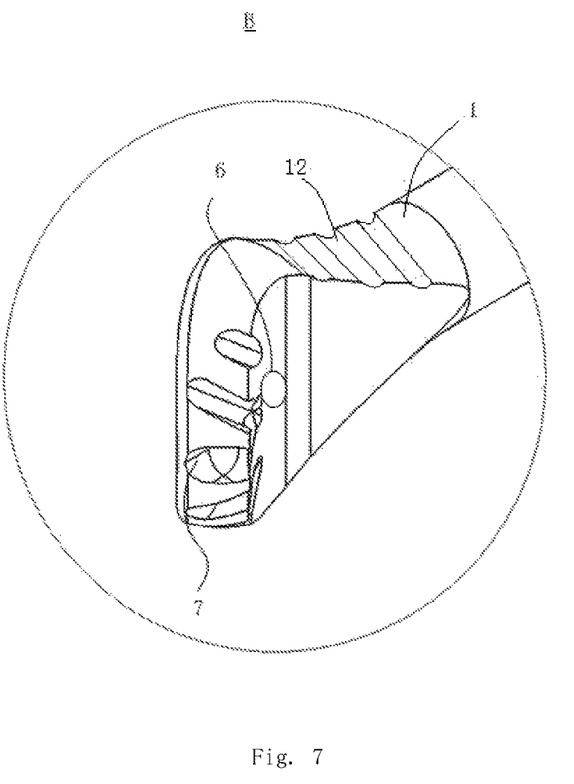
FIG. 7 is a schematic view showing a local enlarged structure of part B shown in FIG. 3, according to another embodiment.

In some embodiments of the present invention, as illustrated in FIG. 7, at least one of two opposed side walls of the end portion 1 of the tool bit connected to the convex surface and the concave surface respectively is provided thereon with a plurality of first grooves 12 spaced from each other. The plurality of first grooves 12 define friction patterns so as to allow the tool bit 100 to have an effect of grinding the bone, and the side wall of the end portion 1 of the tool bit may be used to cut the bone to improve the convenience of use of the tool bit 100. Preferably, each of the first grooves 12 extends in a direction from the spoon center to the spoon bottom and the plurality of first grooves 12 are distributed in a direction from the front to the rear. In this way, the number of the first grooves 12 may be increased to improve the effects of cutting and grinding.

Certainly, the convex surface of the end portion 1 of the tool bit may also be provided with a plurality of second grooves (not shown in figures). The plurality of second grooves define friction patterns to further improve the convenience of use of the tool bit 100. Preferably, each of the second grooves extends in the width direction of the end portion 1 of the tool bit and the plurality of second grooves are distributed in a direction from the front to the rear.

Figure 8:
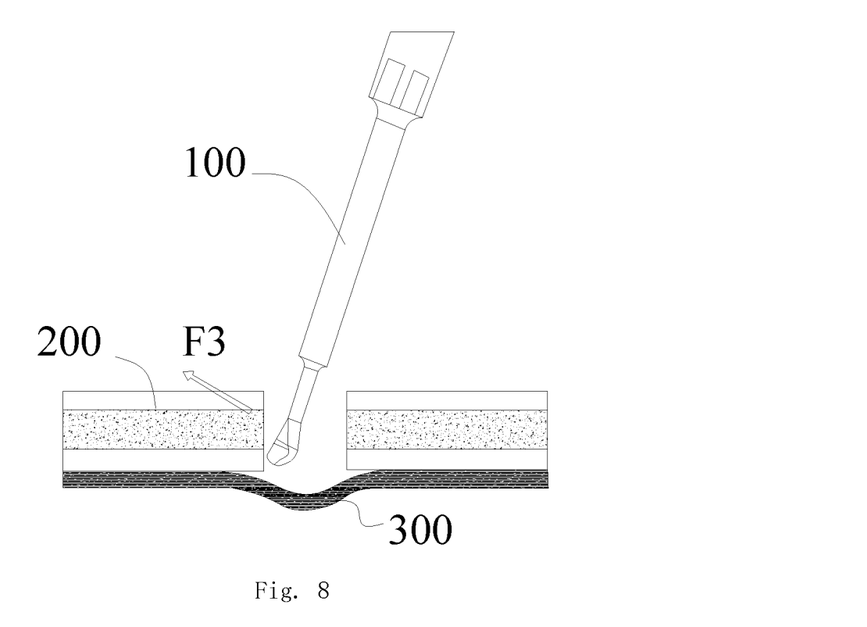
FIG. 8 is a schematic view showing the tool bit of the ultrasonic osteotome in a usage state in accordance with an embodiment of the present invention.
Figure 9:
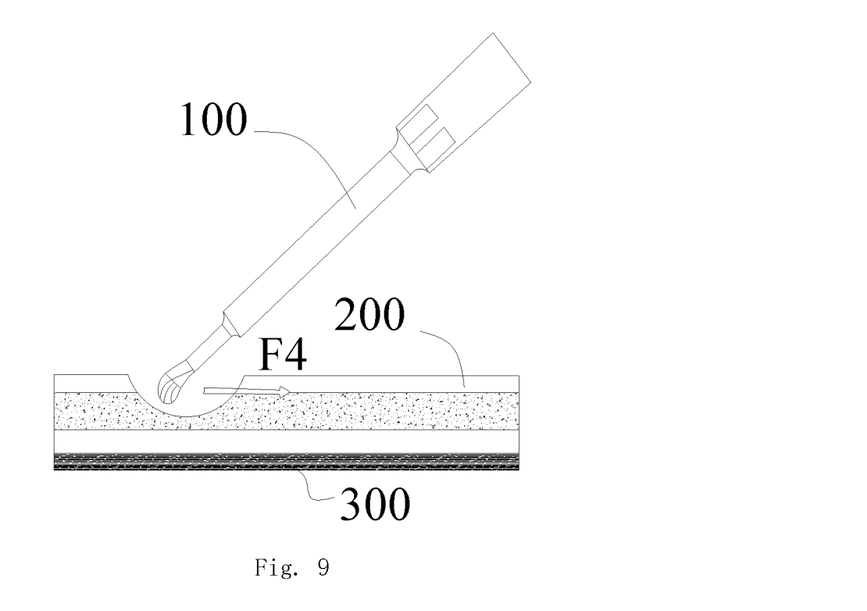
FIG. 9 is a schematic view showing the tool bit of the ultrasonic osteotome in another usage state in accordance with an embodiment of the present invention.

The operation of the tool bit of the ultrasonic osteotome according to an embodiment of the present invention will be described below with reference to FIGS. 8-9. When the tool bit 100 having an end portion with the spoon-like shape according to an embodiment of the present invention is operated, on the basis of the principle of using a spoon, any location of the end portion of the tool bit with the spoon-like shape may be used to remove the bone 200. The operator may arbitrarily select any desired manipulation or posture without being limited in operation. It may be used easily. In use, the end portion 1 of the tool bit with the spoon-like shape may extrude into between the spinal dural and the vertebral body (bone) to be removed, and a force may be applied in a direction from inside to outside, as shown in FIG. 8. In this way, the chance of hurting the soft tissues 300 such as spinal cord (marrow) accidently may be reduced. Thus, the surgery risk is reduced and the difficulty of operation is also reduced. In addition, in surgery, by means of cleaning and cooling function of the poured liquid flowing from the bore 6, the spoon center/spoon bottom, the entire end portion 1 of the tool bit and the tissue they contact with may be cleaned and cooled by the poured liquid in real time completely, so as to ensure the bone crumbs (not shown) removed from the bone 200 to be discharged timely. Thus, there is a clear and clean view at the incision and the tissue to be remained is protected from being damaged.

In accordance with an embodiment of the present invention, it further provides an ultrasonic osteotome comprising the tool bit as described in any of the above embodiments. Such design of the ultrasonic osteotome according to the embodiment of the present invention, not only may increase the cutting speed to reduce the time required for surgery, but also can be positioned correctly in cutting operation without skidding to improve the chance of success in surgery.

In the above description, the terms of "an embodiment", "some embodiments", "exemplary embodiment", "example", "specific example" or "some examples" mean that the specific features, structures, materials or characteristics being described in the embodiment or example may be contained in at least one embodiment or example of the present invention. In the description, the exemplary expression for the above terms is not necessarily limited to the same embodiment or example. And the specific features, structures, materials or characteristics described may be combined in any suitable means in any of one or more embodiments or examples.

Although some embodiments of the general inventive concept are illustrated and explained, it would be comprehended by those skilled in the art that modifications, replacements, alternations and variations may be made in these embodiments without departing from the principles and spirit of the general inventive concept of the disclosure, the scope of which is defined in the appended claims and their equivalents.

What is claimed is:

1. A tool bit of an ultrasonic osteotome, comprising:
an arbor; and
an end portion of the tool bit connected to a front end of the arbor;
wherein:
the end portion of the tool bit has a spoon-like shape and has a toothed front edge;
the front edge of the end portion of the tool bit is formed with a plurality of tooth slots, at least one tooth slot substantially extending in a direction from a concave surface of the end portion of the tool bit to a convex surface thereof; and
each of the tooth slots has an end in communication with the concave surface of the end portion of the tool bit, and has a length reduced gradually from a central part to two lateral parts in a width direction of the tooth slots.

2. The tool bit according to claim 1, wherein the front edge of the end portion of the tool bit has a maximum width not less than the width of the arbor.

3. The tool bit according to claim 1, wherein both the arbor and the end portion of the tool bit have hollow inner chambers that are communicated with each other.

4. The tool bit according to claim 3, wherein the end portion of the tool bit is formed with bore(s) which is(are) located in at least one of a spoon center and a spoon bottom of the end portion of the tool bit and is(are) in communication with the hollow inner chambers.

5. The tool bit according to claim 3, further comprising:
a bit body connected to a rear end of the arbor,
wherein the arbor and the bit body are of cylindrical shape, the bit body has a cylindrical dimension greater than that of the arbor, and the bit body and the arbor are connected via an arc transition.

6. The tool bit according to claim 5, wherein the bit body is provided with a wrench-operation position.

7. The tool bit according to claim 6, wherein a threaded connection hole is formed on a side of the bit body opposed to the arbor and is communicated with the hollow inner chambers.

8. The tool bit according to claim 1, wherein each of the tooth slots is at an angle of less than 90 degrees with respect to the direction from the concave surface of the end portion of the tool bit to the convex surface thereof.

9. The tool bit according to claim 1, wherein at least one of two opposed side walls of the end portion of the tool bit connected to the convex surface and the concave surface respectively is provided with a plurality of first grooves spaced from each other.

10. The tool bit according to claim 9, wherein each of the first grooves extends in a direction from a spoon center to a spoon bottom and the plurality of first grooves are distributed in a direction from a front to a rear.

11. An ultrasonic osteotome comprising the tool bit according to claim 1.

* * * * *